(12) United States Patent
Azad (10) Patent No.: US 9,168,101 B2
(45) Date of Patent: Oct. 27, 2015

(54) APPARATUS AND METHOD FOR STERILIZATION AND ORGANIZATION OF A TAMPER RESISTANT LOCK AND RECEPTACLE

(71) Applicant: Morris Azad, Beverly Hills, CA (US)

(72) Inventor: Morris Azad, Beverly Hills, CA (US)

( * ) Notice: Subject to any disclaimer, the term of this patent is extended or adjusted under 35 U.S.C. 154(b) by 526 days.

(21) Appl. No.: 13/630,158

(22) Filed: Sep. 28, 2012

(65) Prior Publication Data

US 2014/0092937 A1   Apr. 3, 2014

(51) Int. Cl.
| | |
|---|---|
| *B65B 55/02* | (2006.01) |
| *B65B 31/00* | (2006.01) |
| *B65D 69/00* | (2006.01) |
| *B65D 73/00* | (2006.01) |
| *A61B 19/02* | (2006.01) |
| *G01K 11/12* | (2006.01) |
| *A61B 19/00* | (2006.01) |

(52) U.S. Cl.
CPC .............. *A61B 19/026* (2013.01); *G01K 11/12* (2013.01); *A61B 2019/024* (2013.01); *A61B 2019/0209* (2013.01); *A61B 2019/0213* (2013.01); *A61B 2019/0235* (2013.01); *A61B 2019/0244* (2013.01); *A61B 2019/0267* (2013.01); *A61B 2019/307* (2013.01)

(58) Field of Classification Search
CPC ........... A61L 2/00; A61L 2/206; A61L 12/00; B65B 55/02
USPC .................... 53/425, 434, 473; 422/294, 305; 206/570–572, 484
See application file for complete search history.

(56) References Cited

U.S. PATENT DOCUMENTS

| | | | |
|---|---|---|---|
| 2,741,559 A | 4/1956 | Banowitz | |
| 3,604,616 A | 9/1971 | Greif | |
| 3,861,521 A * | 1/1975 | Burtz | ............................ 206/63.3 |
| 3,941,528 A | 3/1976 | Cotterell | |
| 4,046,254 A | 9/1977 | Kramer | |
| 4,188,443 A | 2/1980 | Mueller et al. | |
| 4,358,015 A * | 11/1982 | Hirsch | .......................... 206/439 |

(Continued)

FOREIGN PATENT DOCUMENTS

WO       2011/131953 A1    10/2011

OTHER PUBLICATIONS

International Search Report and Written Opinion of the ISA.

*Primary Examiner* — Monzer R Chorbaji
(74) *Attorney, Agent, or Firm* — Trojan Law Offices (57) ABSTRACT

A multicompartment envelope or sterilization receptacle for receiving and storing medical instruments includes an adhesive flap for sealing multiple compartments within a single envelope. Individual compartments within the multicompartment enveloped can be opened while still keeping the seal of other compartments, thus keeping unused instruments sterilized. The multicompartment envelope or sterilization receptacle has an aperture for insertion of a heat-deforming color changing sterilization indicator device, where, after exposure to extreme heat, the sterilization indicator device deforms and cannot thereafter be inserted or removed from an aperture of a sterilization receptacle fitted for an unsterilized sterilization indicator device. Thus, the practitioner is assured of sterilized instruments in a sterilization receptacle, when an intact, color changed sterilization indicator device is within the aperture of the sterilization receptacle. Several multicompartment envelopes can further be organized within a binder by procedure or instrument type.

7 Claims, 6 Drawing Sheets

(56) References Cited

U.S. PATENT DOCUMENTS

| | | |
|---|---|---|
| 4,438,222 A | 3/1984 | Nakagawa et al. |
| 4,520,958 A | 6/1985 | Jones et al. |
| 4,601,588 A | 7/1986 | Takahara |
| 4,960,204 A | 10/1990 | Young et al. |
| 5,267,646 A | 12/1993 | Inoue et al. |
| 5,730,530 A | 3/1998 | Stoddard et al. |
| 5,732,821 A | 3/1998 | Stone et al. |
| 5,918,740 A | 7/1999 | Berry |
| 5,947,296 A | 9/1999 | Castora |
| 6,123,188 A | 9/2000 | Ahonen |
| 6,155,423 A | 12/2000 | Katzner et al. |
| 6,439,625 B1 | 8/2002 | Schainholz et al. |
| 6,536,190 B1 | 3/2003 | Webb et al. |
| 6,619,843 B2 | 9/2003 | Harmanoglu |
| 7,029,178 B2 | 4/2006 | Gzybowski |
| 7,192,640 B2 | 3/2007 | Holbert et al. |
| 7,540,776 B2 | 6/2009 | Graeve et al. |
| 7,870,959 B2 | 1/2011 | Kuo et al. |
| 2004/0178099 A1 | 9/2004 | Natay-Curley |
| 2006/0023974 A1 | 2/2006 | Zimmerman |
| 2008/0029410 A1 | 2/2008 | Dodsworth |
| 2011/0250104 A1 | 10/2011 | Martel et al. |
| 2012/0181200 A1* | 7/2012 | Hulliger ................ 206/438 |
| 2012/0267272 A1 | 10/2012 | Agrawal |

* cited by examiner

APPARATUS AND METHOD FOR STERILIZATION AND ORGANIZATION OF A TAMPER RESISTANT LOCK AND RECEPTACLE

FIELD OF THE INVENTION

The present invention relates generally to sterilization receptacles and tamper resistant devices, and more particularly, to a multicompartmented sterilization receptacle and sterilization indicator device, which aid in organization, and prevent post sterilization tampering of instruments, especially in the fields of medicine, dentistry, and laboratory arts.

BACKGROUND OF THE INVENTION

Surgical instruments used in medical and dental practice are often stored in sealed envelopes or other containers. Other fields where sterilized instruments and equipment are desired include research laboratories, crime laboratories, and in the practice of veterinary medicine. Envelopes or other containers storing contaminated instruments undergo a sterilization process and are capable of withstanding extreme heat and have gas permeability to allow for the sterilization of the instruments. Instruments undergoing this extreme heat (autoclaving) and/or chemical treatment (chemiclaving) may be used on different patients without risk of contaminating a new patient with diseases from a previous patient who had the same instruments used on him or herself because the instruments are sterilized after exposure to this extreme heat and/or chemicals.

Commonly, in current practice, one or more unsterilized instruments are placed into a single compartment in an autoclaving receptacle. When this compartment is opened, the practitioner uses the needed sterilized instruments, and any instruments not used immediately become unsterilized, and not fit for use because they have been exposed to the unsterile environment. The unused instruments, if they are to be used on future patients, need to be resterilized in order to be fit for use. However, practitioners run the risk of using unsterilized instruments on a patient even when the instruments are located in a receptacle that has markings (such as activated autoclave tape) that indicate that the container is sterile because current methods of marking sterilized packages do not necessarily indicate that the objects within the receptacle are sterilized, only that the sterilization indicator underwent sterilization.

Indicating inks, such as chemically reactive inks or heat reactive inks are available that change color on exposure to sterilizing chemicals, or upon exposure to heat such as those disclosed in U.S. Pat. No. 4,601,588 to Takahara et al. However, the mere use of sterilization indicator devices does not verify that the instruments inside of the sterilization receptacle were there during sterilization and subjected to the sterilization process. This can occur for several reasons, one of which is that as most containers let users seal or lock the container at any time, even after sterilization has taken place, as shown by the sterilization locking device in U.S. Patent Appl. Pub. No. 20110250104 by Martel et al., where a sterilization lock can be closed after sterilization has taken place. In another type of sterilization system, as disclosed in U.S. Pat. No. 7,870,959 to Kuo et al., sterilization inks are directly printed on a sterilization envelope. While the heat changed ink indicates that the envelope has undergone sterilization, instruments can be inserted into the envelope after the envelope has undergone sterilization. This is how one can abuse and defraud currently available sterilization systems. In cases of pouches and envelopes, an empty and unsealed pouch can be placed in an autoclave until its indicator changes color, then the pouch or envelope is removed from the autoclave, filled with unsterilized instruments and sealed. Unsterilized instruments can be placed into a sterilized pouch and sealed after the envelope, but not instruments, has undergone sterilization. This color change indicator device would lead others to believe that the items in the pouch are sterilized, when in fact, they are not.

In cases of containers that use sterilization locks with heat sensitive ink printed directly on the lock, the user can place only the lock in the autoclave to have the color change, and then apply these locks to any unsterilized container to have the container and contents within the container appear sterilized. In this circumstance, unsterilized instruments are in a locked container that appears to have been sterilized, even though it is only the sterilization lock that has been sterilized. An unscrupulous user can sterilize hundreds of sterilization indicator devices and lock containers with these devices, without actually sterilizing any instruments, thus deceiving others that the contents are sterile.

Along with the above-mentioned deficiency, another deficiency of single compartment sterilization envelopes is that once the sterilization process has been completed, keeping sterilized instruments organized is difficult. The practitioner or user will have tens, if not hundreds of individual envelopes, each having a single, or a few small instruments. Envelopes may easily be lost or misplaced because of the vast number of envelopes needed in medical, dental, or laboratory procedures. Another disadvantage is that health monitoring agencies such as OSHA, dental boards, and medical boards require that each envelope show the date of sterilization. For practitioners and labs who do many procedures a day, it is cumbersome to date, sort, label, and place sterilization indicators on each envelopes, and should they choose to place multiple instruments in a single pouch to save time and cost, it would lead to the problem of exposing all instruments within pouch to an unsterile environment upon opening the pouch even when only one single instrument from that pouch is needed. The rest of the instruments within the opened pouch, if not used immediately, cannot be used on a different patient until resterilized.

Thus there is a need for sterilization containers modified for better organizing of medical instruments as well and tamper resistant devices to prevent unsterilized medical instruments from appearing sterilized.

SUMMARY OF THE INVENTION

In one embodiment, a multicompartmented envelope for sterilization is disclosed. The envelope retains medical or dental instruments before, during and after sterilization. The envelope has a plurality of compartments, each compartment holding one or a few instruments. The envelope has a first layer of a flexible sheet material, such as plastic or paper, and a second layer of flexible sheet material. The first and second layers are dimensionally similar to each other and overlap each other. When these layers are secured together at a plurality of lines, the secured areas form pockets, or compartments with the first layer forming back of the compartment and the second wall forming the back of the compartment. The secured areas form closed edges along each compartment, and there are at least two closed edges along the periphery of each compartment. There is an unsecured area of each compartment on one of the edges of the periphery which provides a space for insertion of instruments.

A flap or cover having an adhesive side facing the two layers is placed over the first and second layer covering all open edges of the compartments. This flap seals the open side(s) of each compartment, and thus a single adhesive flap is able to seal a plurality of compartments. The arrangement of the multiple compartments and the adhesive flap allow instruments from individual compartments to be retrieved by opening one compartment with sterilized instruments without opening other compartments having sterilized instruments. This allows the user to keep some instruments sterilized in the multicompartment envelope while retrieving other instruments for immediate use. Retrieval of the instruments can be accomplished by preferably puncturing the first layer of a compartment holding an instrument. Due to the sealed edges of the compartments, puncturing the first layer only exposes the contents of that single compartment, while leaving the instruments within other compartments entirely sealed.

The flexible sheet material of the envelope is made from a material that is permeable to dry heat, steam, and sterilization gases, while being impervious to contaminants. It may be made of paper, plastic, or a combination or paper and plastic materials and able to withstand temperatures of at least 121° C. in an autoclave. The multicompartmented envelope also may have an indicator ink pre-printed on the envelope, or sterilization indicator tape attached to it.

To aid in organization of instruments, the multicompartment envelope may have apertures near an edge such that the multicompartment envelopes can be inserted into a ringed binder. A system for organizing several multicompartment envelopes by procedure type or instrument type has several multicompartment envelopes in a ringed binder, and the multicompartment envelope having apertures for placement of the envelopes into the binder that has aligned rings to insert the plurality of envelopes. A plurality of dividers or tabs can be placed between groups of multicompartment envelopes, which can be grouped by type of procedure or type of instrument. By having the multicompartment envelopes arranged by instrument type or procedure type, this allows the practitioner to pull out a single envelope for a procedure, knowing that all instruments needed for that procedure are within that envelope. This is in contrast to a non-multicompartment envelope, where the practitioner would have to search for several instruments, each in separate envelopes, which may be scattered and unorganized.

In another embodiment, a sterilization indicator device is disclosed. The sterilization indicator device has a sterilization pin, which has a proximal end with a tapered region for insertion through an aperture on a sterilization envelope. The proximal end is made from a heat-deformable material that deforms when the temperature in the autoclave reaches a certain threshold. The sterilization pin also has a distal end with an enlarged region of cross-sectional area greater than the diameter of the aperture. This enlarged region prevents the sterilization indicator from passing all the way through the aperture. The sterilization indicator device also has a heat sensitive color indicating composition which color after exposure to heat in an autoclave. The proximal end of the sterilization pin deforms when heated, which creates a deformed proximal end. The deformed proximal end has a cross sectional area greater than that of the aperture, and therefore prevents the sterilization pin from being withdrawn from the aperture after it has been heated and deformed. The purpose of the pin is that once the pin is inserted into the aperture of the sterilization container or envelope, and it deforms, the pin cannot be removed without breaking it, so the practitioner is assured that envelope or container with an intact deformed pin has not has been opened.

In one embodiment, the sterilization pin is inserted within an aperture of a multicompartment envelope before sterilization. The pin snaps into the aperture due to a beveled or winged design of the pin, which makes it easy to insert into the aperture, but difficult to withdraw. The aperture spans both the first layer, second layer and adhesive flap of the multicompartment envelope. After exposure to extreme heat, the sterilization pin changes color and deforms. This deformed pin is unable to be withdrawn from the aperture. A deformed pin that has not previously been inserted into the aperture before the container was sterilized is unable to be inserted into the aperture because of its changed shape. This inability to insert a deformed pin into the aperture of a sterilization envelope prevents an unscrupulous practitioner from sterilizing a pin by itself, and then, after sterilization of the pin, trying inserting the pin into the aperture of an unsterilized envelope. If an unscrupulous user were able insert sterilized pins into these envelopes, it would deceive users into believing that the envelope itself underwent sterilization, when in fact, only the pin underwent sterilization.

A deformed, color changed pin within the aperture of the multicompartment envelope necessarily means that the pin was placed within aperture before sterilization, and that both the pin, the envelope, and the contents of the envelope, underwent sterilization together.

In another embodiment of a sterilization pin, the sterilization pin prevents a sterilization receptacle from being opened unless the pin is fractured broken. The pin proximal end of the pin deforms after exposure to heat creating a cross sectional deformed area wider than that of the aperture of the receptacle, thus preventing the pin from being withdrawn through the aperture, where it was inserted before sterilization. Because the pin is deformed, it cannot be withdrawn through the aperture and must be fractured to retrieve the contents of the sterilization receptacle. An intact, color changed, deformed sterilization pin within the aperture of the sterilization receptacle locking two parts of a sterilization receptacle together verifies that the closed sterilization receptacle with an intact sterilization pin has not been opened. The only way to retrieve instruments for immediate would be to break the pin, since the intact deformed pin cannot be withdrawn through the aperture. A practitioner who sees a broken pin knows that the receptacle has likely been opened, and the contents are not sterile. Additionally, a deformed pin that has undergone sterilization without previously being inserted into the aperture cannot thereafter be inserted into the aperture of an unsterilized container since the head of the deformed pin will not fit through the aperture of the sterilization receptacle.

In another embodiment of a sterilization pin, to aid the user in breaking the pin to open the receptacle, the pin may have a weakened area in the shaft (such as a tapered, slotted, or notched region) of reduced thickness compared to other regions of the shaft, thereby allowing the user to twist, pull, cut, or snap the pin off, thereby allowing the user to open the receptacle. In still another embodiment, the sterilization pin is inserted into a slidable pin locking device on a sterilization container. This feature prevents the container from being opened once the sterilization pin has been inserted unless the pin shaft is broken. In other embodiments, the pin locking device may have built in devices (such as a blade) that, once aligned with a weakened area of the shaft, aid in cutting the shaft of the pin, thereby allowing the practitioner to open the container. If the blade is not aligned with the weakened part of the shaft, the blade will not be able to cut the shaft, and the container will remain sealed and locked.

A method of sterilizing instruments is disclosed, where the method comprises placing unsterilized instruments into sterilization receptacle, sealing the receptacle, inserted a sterilization indicator device through an aperture of the receptacle when the receptacle is in a closed position and exposing the sterilizing receptacle to sterilizing heat conditions.

BRIEF DESCRIPTION OF THE DRAWINGS

These and other features and advantages of the present invention will become appreciated as the same becomes better understood with reference to the specification, claims and drawings herein:

DETAILED DESCRIPTION OF THE DRAWINGS

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

Figure 1A:
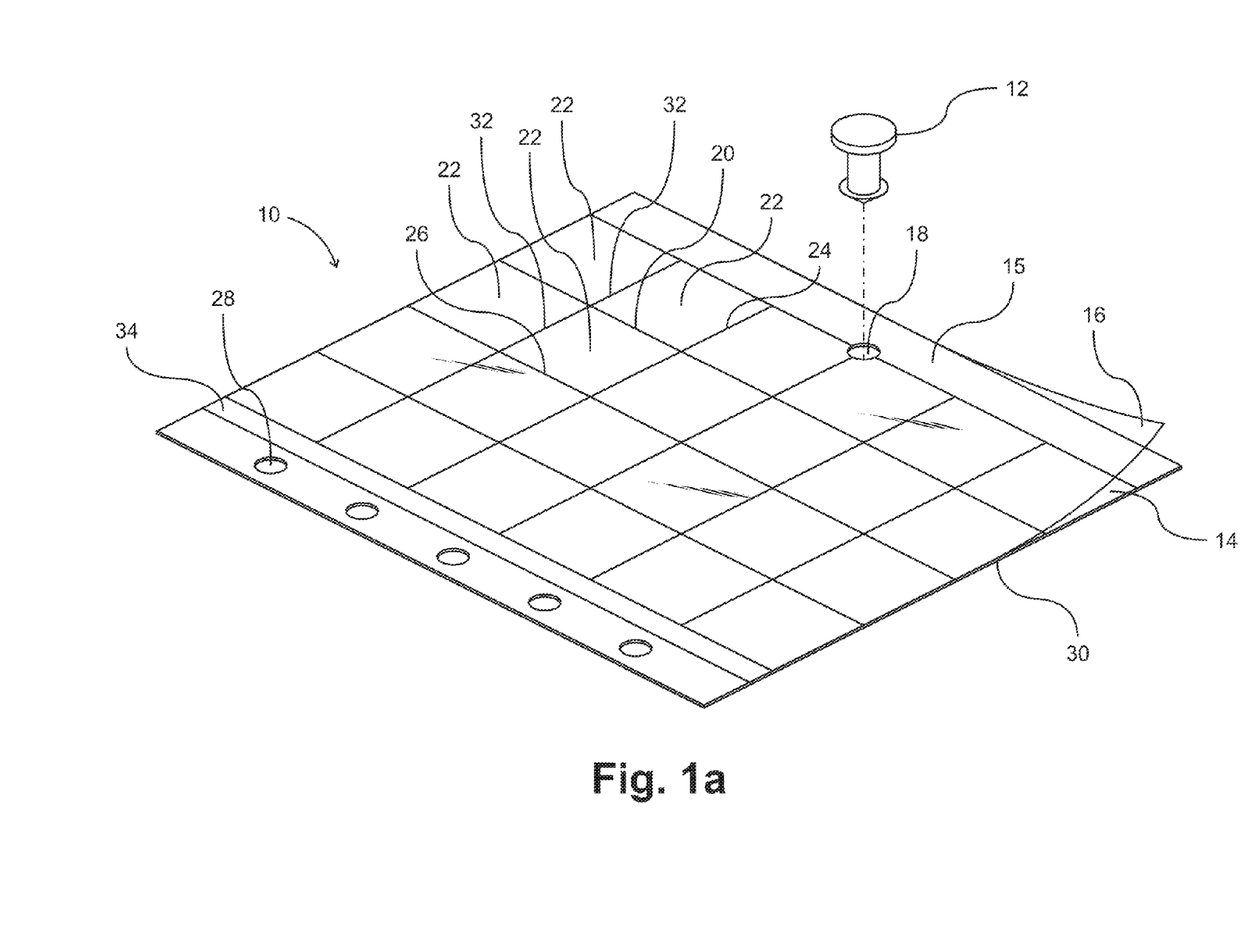
FIG. 1a is a perspective view of a multicompartment envelope for sterilization.
Figure 1B:
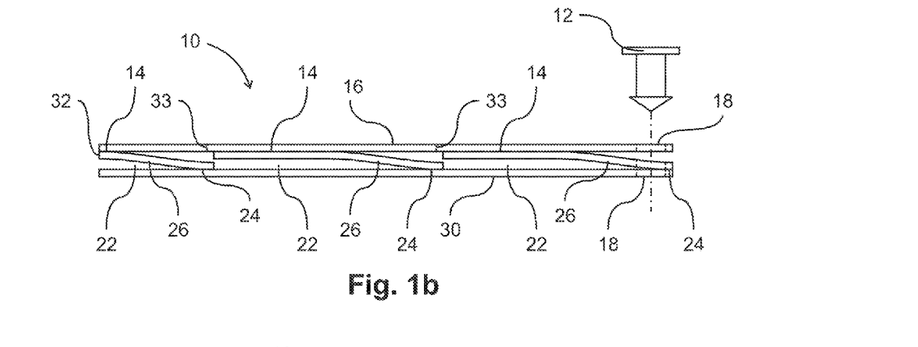
FIG. 1b is cross sectional view of a portion of a multicompartment envelope covered with an adhesive flap.

FIGS. 1a and 1b illustrate a multicompartment envelope 10 for use in sterilization of instruments such as medical or dental instruments. The envelope has a series of compartments 22 or pouches where instruments can be inserted. The envelope is made of a first layer 30 of a flexible sheet material such as, but not limited to, paper or plastic. A second layer 14 of a flexible sheet material is dimensionally similar to the first layer 30 and overlaps the first layer 30. The first layer 30 and second layer 14 are secured together at a plurality of locations that form secured compartment side wall edges 20, 26, and compartment bottom edges 24. These edges may be of uniform or non-uniform sizes and shapes to fit different instruments, and therefore the grid lines may be spaced at various distances from each other. In this embodiment, there are three edges, however, compartments with two edges, such as the bottom portion of the compartment disclosed in the embodiment of U.S. Pat. No. 4,358,015 to Hirsch, may also be used. The first layer 30 and second layer 14 may be secured to each other by a variety of means, including chemical or physical bonding (such as heat, chemical, or adhesive sealing). A compartment top edge 32 is open (i.e. not secured), for insertion of instruments into the compartments 22.

One or more than one instrument may be inserted with an individual compartment 22. Each multiple compartment envelope 10 may have a few individual compartments (as few as two or four) or can have several compartments (such as thirty or more), depending on the size and number of instruments the practitioner wishes to have in a single multicompartment envelope 10. For example, scalpels may need large compartments, and therefore a multicompartment envelope 10 with scalpels may have only a few compartments, while multicompartment envelopes for small drill bits would require only small compartments, and each multicompartment envelope could fit 30 or more compartments. The number of individual compartments and the size of the compartments in a multicompartment envelope can be designed for specific procedures, and multicompartment envelopes can be designed for holding one specific kind of instrument for easy organization of instruments either by type of instrument or type of procedure.

Also on the multicompartment envelope is an adhesive flap 16, which has dimensions substantially similar to the dimensions of the first layer 30 and second layer 14. The adhesive flap or cover 16 is secured to the multicompartment envelope 10 via either the first layer 30 or second layer 14. Preferably, the adhesive flap or cover 16 has an edge integrated with an edge of first layer 30 or second layer 14 that allows the flap 16 to be either in an open or closed position relative to the first layer 30 and second layer 14. The flap 16 has an adhesive side that permanently bonds to the second layer 14 when the adhesive side is pressed against the second layer 14 to seal each open edge 32 of each compartment 22. This sealing prevents communication between the compartments with each other and the outside unsterile environment.

The adhesive flap 16 may include a non-adhesive liner that covers the adhesive flap 16 which prevents the adhesive flap 16 from adhering to the first layer 30 and second layer 14 inadvertently, and only adheres to the first layer 30 and second layer 14 after the non-adhesive liner is removed. A non-adhesive liner, which may be a peelable release strip, is disclosed in U.S. Pat. No. 4,358,015 to Hirsch, which is fully incorporated by reference herein. The adhesive side of the adhesive flap 16 may be entirely or partially coated with an adhesive, but at a minimum, the adhesive is placed such that it seals the open edge 32 of each compartment 22. The adhesive flap 16 may be made of a substance used for packaging medications as described in U.S. Pat. No. 7,192,640 to Holbert et al., or U.S. Pat. No. 6,155,423 to Katzner et. al, which are fully incorporated by reference herein.

This adhesive flap 16 seals each compartment 22 such that any instruments within an individual compartment 22 cannot be retrieved without breaking, tearing, or cutting either the first layer 30 alone, or second layer 14 and adhesive flap 16 together. Preferably, instruments can be retrieved by breaking the first layer 30, or by breaking a combination of the second layer 14 and adhesive flap 16. By opening compartments in this manner, instruments from individual compartments 22 can be retrieved without opening (and making unsterile) instruments in other compartments. Breaking portions of the first layer 30, or second layer 14 and adhesive flap 16 can be accomplished by twisting, pinching, or puncturing a portion of the area that the user desires to open. Optionally, the portions first layer 30, second layer 14 or adhesive layer 16 may be scored or have a perforation 33 to ease in opening a compartment.

In another embodiment, pull tabs or other devices may be adjacent to the first layer 30, second layer 14, or adhesive flap 16 that aid in opening individual compartments by opening a compartment when a tab is pulled, while leaving other compartments intact. The adhesive flap 16 can be opened at specific locations which exposes the contents of one compartment without breaking open the adhesive flap at other locations, thus keeping sealed compartments where the adhesive flap 16 is not torn or broken, and only opening compartments where the user intends to open one particular compartment, and retrieve the instruments for immediate use. This has the advantage of keeping instruments in unopened compartments sterile, while allowing the practitioner retrieve particular instruments in one compartment without the risk of contaminating instruments in the unopened compartments.

Described now is a sterilization pin 12 for insertion into a multicompartment envelope to verify that contents of the multicompartment envelope are sterile. Within the adhesive flap 16 and through both the first wall 30, second wall 14 and adhesive flap 16 is an aperture 18 for placement a sterilization pin 12. The sterilization pin 12, made from a heat-deformable thermoplastic, which becomes deformed after exposure to heat during sterilization. Thermoplastic materials may be polyvinyl chloride or polystyrene, such as the deformable thermoplastics disclosed in U.S. Pat. No. 4,188,443 to Mueller et al., U.S. Pat. No. 6,439,625 to Schainholz et al., U.S. Pat. No. 7,540,776 to Graeve et al., U.S. Pat. No. 4,438,222 to Nakagawa et al., and U.S. Pat. No. 3,941,528 to Cotterell, which are fully incorporated in their entirely by reference herein. The temperature in an autoclave must be at least 121° C. or higher for proper sterilization of instruments, and typically go as high as 134° C. Thus, either the indicating ink changes color and/or the thermoplastic deforms in this temperature range to indicate to the practitioner that the pin 12 has undergone sterilization.

An intact sterilization pin 12, which has undergone heat sterilization, changes color due to the inclusion of a heat indicating composition within the pin 12. After the pin 12 has been deformed, the pin 12 is prevented from being withdrawn from the aperture 18. This deformation also prevents a sterilized pin 12 from entering the aperture 18 if it were not inserted before deformation. The pin 12 provides several advantages to aid the user in verification of sterilized devices. First, since a deformed pin cannot be inserted into the aperture 18 after the pin 12 has been sterilized, the pin 12 cannot be sterilized and then fraudulently inserted into the aperture 18 of an envelope having unsterilized contents. In this embodiment, the deformed pin is irretrievable situated within the aperture 18, and indicates to the user that all unopened compartments in the multicompartment envelope 10 have been sterilized. A deformed pin within the aperture verifies that the sterilization pin 12 was inserted through the aperture 18 before the multicompartment envelope 10 was sterilized, and that the contents of each unopened compartment are sterile. The deformed pin 12 therefore acts as a permanent visual signal within the multicompartment envelope 10 that the contents of the multicompartment envelope 10 are sterile. In this embodiment, the deformed pin is not removed (by breaking, or by other means) to access sterilized instruments within multicompartment envelope 10, while in other embodiments the sterilization pin must be broken to open sterilization container (see description and embodiments of FIGS. 4-7).

In the embodiment shown in FIG. 1, the multicompartment envelope 10 has have a series of binder apertures 28 aligned along one edge of the multicompartment envelope 10 to allow the multicompartment envelope 10 to be stored in ringed binders. This allows the practitioner to simply store hundreds of dental instruments in a binder that can be easily sorted and organized. Optionally, additional indicators of heat sterilization can be placed on the multicompartment envelope 10, such as autoclave tape 34. Each multicompartment envelope has one or more notation areas 15 to note the date of sterilization, and any remarks of the contents of the sterilization envelope 10 that the practitioner wishes to include.

Figure 2A:
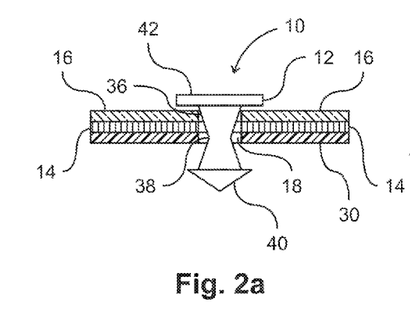
FIG. 2a is cross sectional view of a multicompartment envelope with a tapered shaft sterilization pin through three layers of the multicompartment envelope.
Figure 2B:
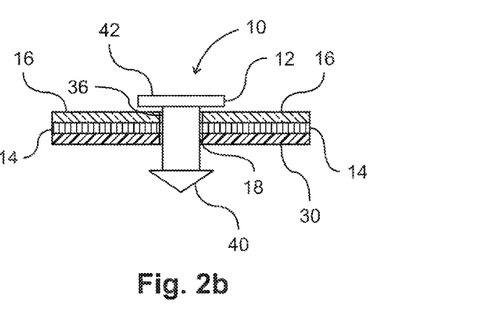
FIG. 2b is cross sectional view of a multicompartment envelope with a straight shaft sterilization pin through three layers of the multicompartment envelope.

FIG. 2a and FIG. 2b depict cross sectional views of a sterilization pin 12 extending through the first layer 30, second layer 14, and adhesive flap 16 of the multicompartment envelope 10 through an aperture 18. In FIG. 2a, the pin has a proximal end 40 having a tapered region for insertion through the aperture 18, which is made from a heat-deformable thermoplastic, while in FIG. 2b, the shaft of the pin 12 is straight. The pin 12 also has a distal end 42 which has an enlarged region of cross-sectional area greater than the diameter of the aperture 18, thereby preventing the enlarged region 42 from passing through the aperture 18. The pin has a middle shaft region 36 which connects the proximal 40 and distal 42 ends of the pin 12 together. The shaft 36 has a cross sectional area less than that of the aperture 18 so that the pin 12 can enter the aperture 18. In embodiments where the sterilization pin 12 must be broken to access a sterilized compartment, (see description and embodiments of FIGS. 4-7) the pin has an area of reduced thickness within the shaft 36 as shown in FIG. 2a. This allows the pin 12 to break off at a predetermined position so the practitioner can open a sterilization container. The weakened area can be of reduced thickness via tapering, non-tapering, slots, perforations, or other comparable means to weaken a shaft. The pin 12 can be twisted, pulled, snapped, or cut in order to break the pin 12 and retrieve the sterile contents in a sterilization container. In embodiments where the pin 12 remains in the aperture, such as the multicompartment envelope 10 previously described, the pin 12 does not need a weakened area, since the pin is used as an indicator of sterility, and the pin 12 does not need to be broken to retrieve instruments from individual compartments 22. Rather, instead of breaking the pin, instruments are retrieved by puncturing either the first layer 30, or second layer 14 and adhesive flap 16 of individual compartments of the multicompartment envelope 10.

Figure 3A:
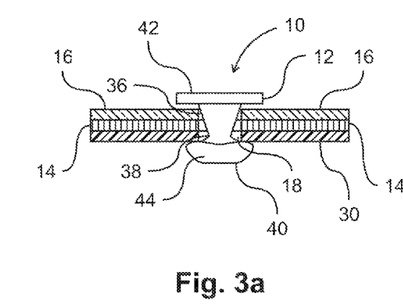
FIG. 3a is cross sectional view of a multicompartment envelope with a sterilization pin through layers of the multicompartment envelope after heat sterilization causes a deformation of a tapered shaft sterilization pin.
Figure 3B:
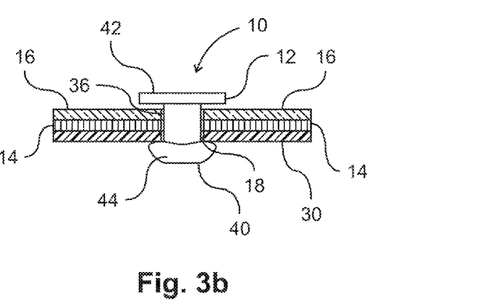
FIG. 3b is cross sectional view of a multicompartment envelope with a sterilization pin through two layers of the multicompartment envelope after heat sterilization causes a deformation of a straight shaft sterilization pin.

FIGS. 3a and 3b depict the same cross sectional views as FIGS. 2a and 2b respectively, except that the multicompartment envelope 10 and pin 12 have undergone heat sterilization and are now deformed. Because the proximal end of the pin 40 is made from a heat-deformable thermoplastic, the proximal end 40 is now a deformed proximal end 44. This deformation results in the cross sectional area of the deformed proximal end 44 having at least a portion greater than the diameter of the aperture 18. The greater cross sectional area of the deformed pin 12 prevents the pin 12 from being withdrawn from the multicompartment envelope 10. If the pin 12 is intact and deformed, the practitioner is assured that the contents in the compartments 22 of a multicompartment envelope 10 were inserted into the compartments 22 before sterilization, contents underwent a sterilization process, and that the container has not been opened. FIG. 3b shows the same cross sectional view as 3a, except that the embodiment of the pin 12 has a straight shaft with no weakened area instead of the tapered shaft embodiment of the pin in FIG. 3a meant breaking.

Figure 4A:
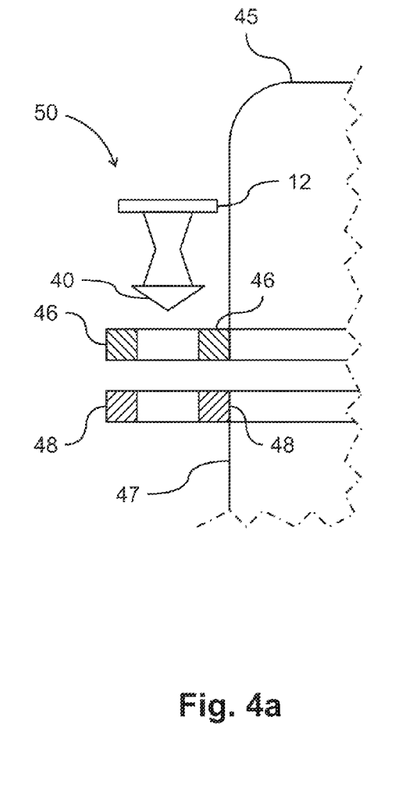
FIG. 4a is cross sectional view of a locking device before a sterilization pin is inserted.
Figure 4B:
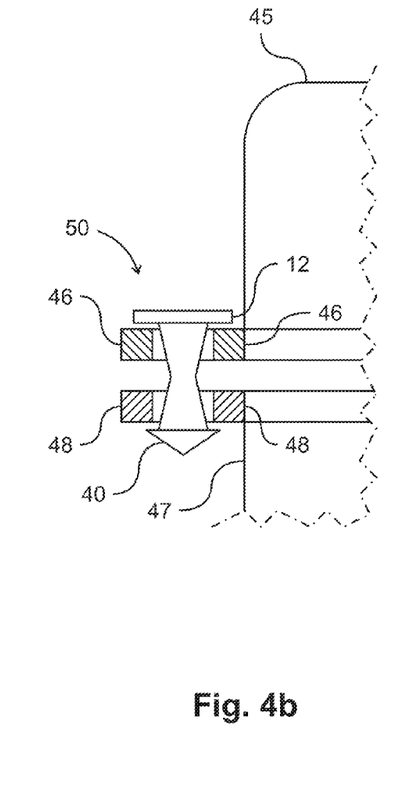
FIG. 4b is cross sectional view of a locking device after a sterilization pin is inserted but before sterilization.
Figure 4C:
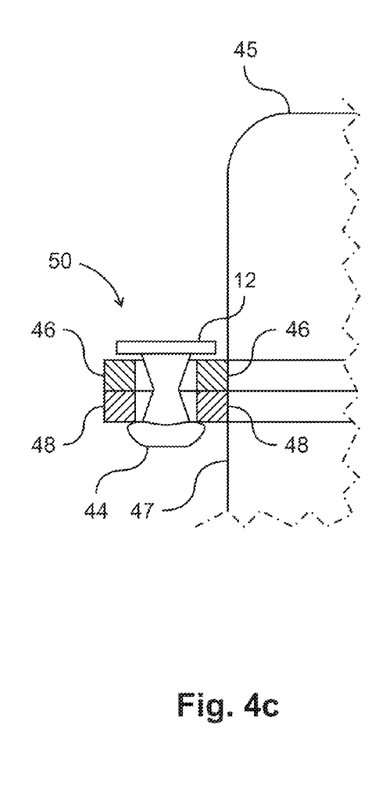
FIG. 4c is a cross sectional view of a locking device after a sterilization pin is inserted and after sterilization.

In contrast to the embodiment of the sterilization pin for a multicompartment envelope 10, where the sterilization pin 12 remains within the aperture 18 of the multicompartment envelope 10, in other embodiments the sterilization pin 12 is used as a locking device that must be broken in order to retrieve the instruments of the sterilization receptacle. FIGS. 4a-c are perspectives of an embodiment of a sterilization pin 12 inserting into a locking device 50 where the pin must be broken in order to retrieve instruments within the sterilization container. The locking device may be a device found on sealing bags such as Zip-lock bags, or other devices, such as ones that have a loop where a lock can be inserted (such as loops where the U of a pad-lock can be inserted). In this embodiment, the pin 12 is inserted through an upper portion 46 and a lower portion 48 of the locking device 50. The upper portion 46 is integral with a top portion of a sterilization container 45. The lower portion 48 is integral to a lower portion 47 of a sterilization container. After heat sterilization, the proximal end 40 of the pin 12 deforms, forming a deformed proximal end 44 and deforms, thus securing the upper 46 and lower 48 portions of the locking device 50 together, which cannot be opened without breaking the pin 12. Only by breaking the pin 12 can sterilization container be opened.

Figure 5:
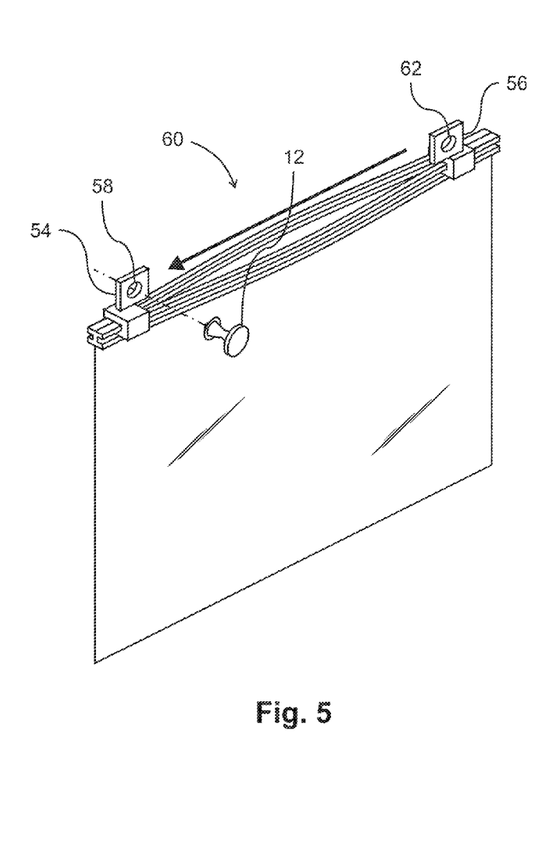
FIG. 5 is a side view of a receptacle having slidable locking devices to seal a receptacle and apertures within the slidable locking device for insertion of a sterilization pin.
Figure 6:
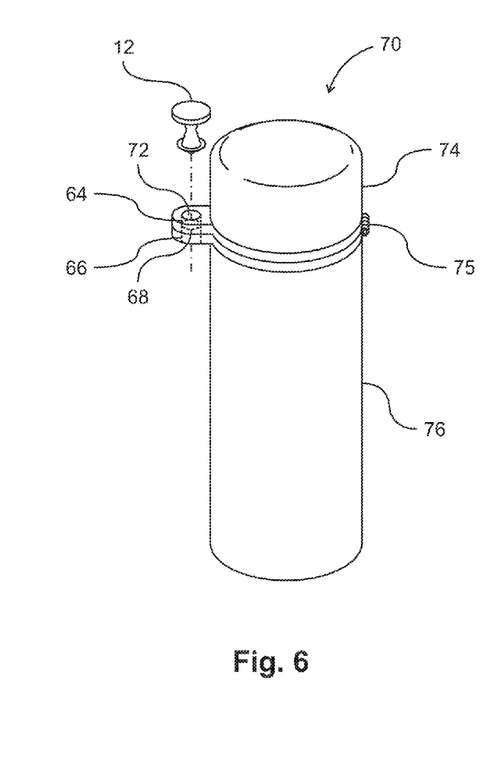
FIG. 6 is a side view of a cylindrical container having locking loops for insertion of a sterilization pin.

FIG. 5 and FIG. 6 depict two embodiments of containers where a sterilization pin 12 can be inserted. A sealable bag 60 having a locking device that slides to seal a bag 60 has a first section of a locking device 54 with a first aperture 58 and a second section of the locking device 56 with a second aperture 62. When the second section of the locking device 56 slides to close the container 60, the two apertures 58, 62 align, allowing the pin 12 to be inserted within these apertures 58, 62. In FIG. 6, a cylindrical container 70 has an upper portion 74 and a lower portion 76 connected to each other via a hinge 75 or other means of connecting two parts of a sterilization container. The upper portion 74 has an upper looped area 64, and the lower portion 76 has a lower looped area 66. The upper and lower looped areas 64, 66 each have an aperture 68, 74 where a pin 12 can be inserted. As described in the preceding sections, after sterilization the pin 12 deforms and the containers 60, 70 can only be opened by breaking the pin 12. If there is no pin, or a broken pin, securing the containers 60, 70, this indicates possible tampering of the sterilized contents of the containers 60, 70. In contrast to a broken pin, an intact deformed color changed pin within the apertures 68, 74 of a sterilization container indicates that the entire receptacle with the pin 12 was sterilized together, since a deformed pin cannot be inserted into the apertures 68, 74. This prevents an unscrupulous user from sterilizing pins first, and then trying to lock unsterilized instruments with a container with these sterilized pins to give the false impression that the contents with the receptacles have also been sterilized.

Figure 7A:
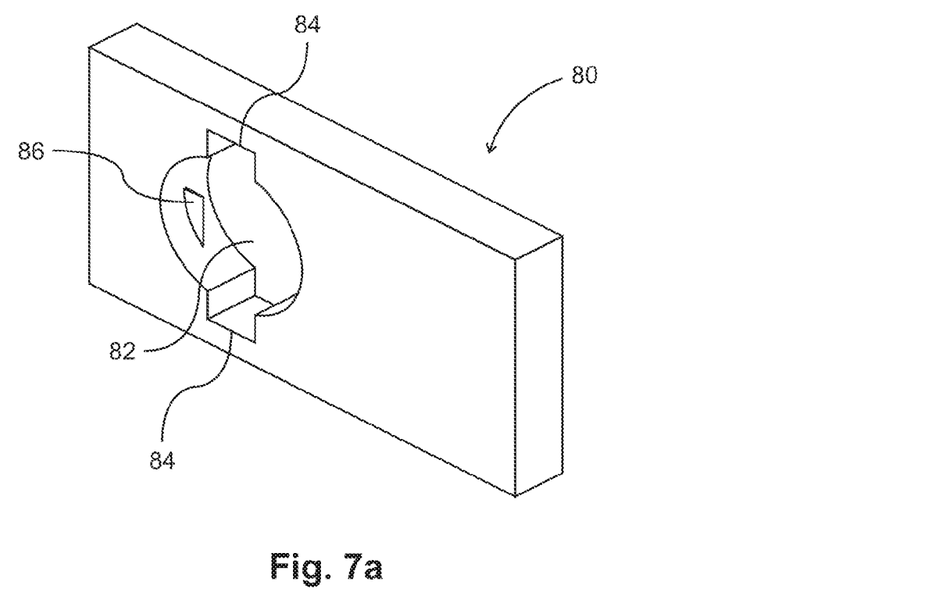
FIG. 7a is a perspective view of moving head of pin locker suitable for receptacles having a slidable sealing device.

FIG. 7a depicts an embodiment of a moving head 80 of a slidable pin locker such as those resembling the slidable sealers of a Zip-lock bag. An example of a sliding locking device is disclosed in U.S. Pat. No. 7,029,178 to Gzybowski, incorporated in its entirety by reference herein. The sliding locking device has a moving head 80 with an aperture 82. The aperture 82 has an upper and lower extensions 84 such that a pin 100 can be inserted through this aperture 82. This aperture 82 is shaped such that the user can only insert the pin 100 in a specific orientation due the shape of the proximal end of the pin 102 and the shape of the aperture 82. The moving head 80 has a blade 86 that is capable of breaking the pin 100 at a predetermined position when the pin 100 is oriented relative to blade 86 at a weakened position 113.

Figure 7B:
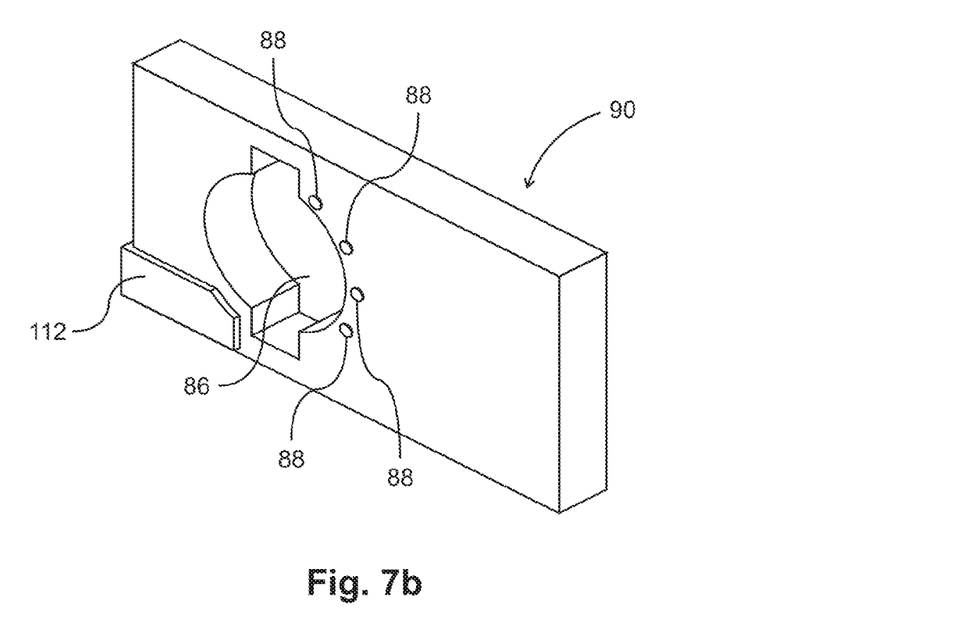
FIG. 7b is a perspective view of stationary head of pin locker suitable for receptacles having a slidable sealing device.

FIG. 7b depicts the stationary head 90 of a slidable pin locker. The stationary head 90 has a matching aperture 86 to the aperture 82 on the moving head 80. In addition, there are a series of indentations or protrusions 88 on the stationary head 90 that align and interlock with the notch or protrusion 110 on the pin 100, similar to how a ratchet catches teeth once a tooth moves past a pawl. By turning the pin 100, with the use of a handle or lever 106, the pin 106 moves in a stepped fashion along the surface of the stationary head 90. The notches or protrusions 110 prevents the pin 100 from turning unintentionally into a position where it is easily breakable (i.e. against the weakened shaft region 113 of the pin 110). A raised surface 112 prevents the pin 110 from being placed upside down in the pin locker.

Figure 7C:
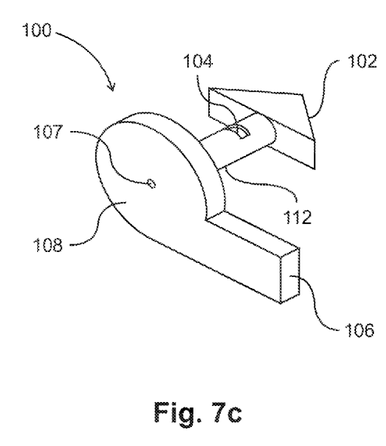
FIG. 7c is a rear perspective view sterilization pin with a handle.
Figure 7D:
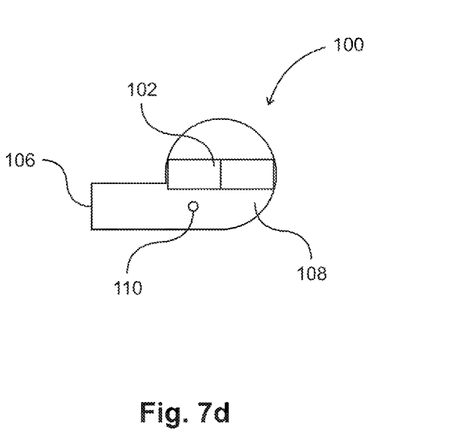
FIG. 7d is a front view of sterilization pin with a handle.

FIG. 7c depicts a perspective view of the pin 100 having a shaft 112, a proximal end 102 and a slotted region 104 that creates a weakened area 113 within the shaft 112. A slotted region 104 is angled on the shaft 112 such that the cross section area of the shaft 112 where the slot 104 is located varies from being as thick as the thickest part of the shaft 112 to a thinner weakened area 113 where the cross section area of the shaft 112 is thinnest. To aid in rotating and locking the pin in the locking device heads 80, 90, a handle or lever 106 is be integral to the distal end 108 of the pin 100. A color changing sterilization indicator 107 is placed on the distal end 108 to indicate when the pin has undergone heat sterilization. FIG. 7d depicts a side view of the sterilization pin 100 with a protrusion tooth 110 to aid in locking the pin 100 to the locking device heads.

Figure 8A:
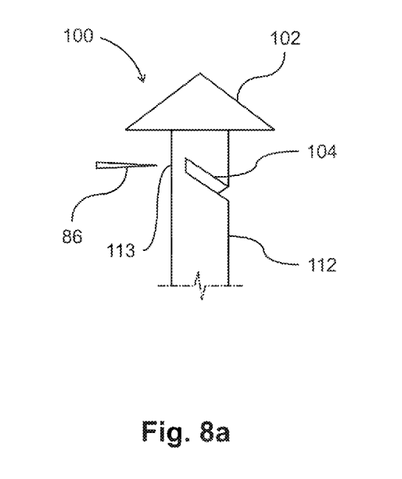
FIG. 8a is a side view of a slotted sterilization pin shaft and cutting blade aligned to a breakable position.
Figure 8B:
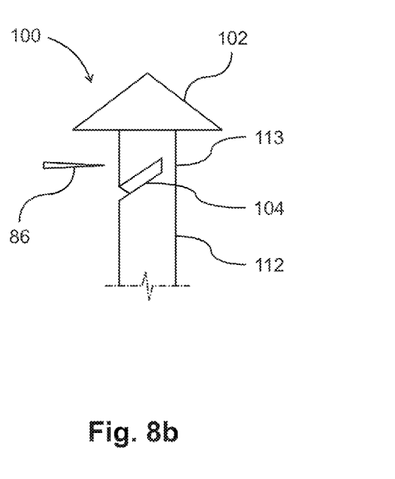
FIG. 8b is a side view of a slotted sterilization pin shaft and cutting blade aligned to an unbreakable position.

To properly insert the pin 100 through the stationery head 90 and moving head 80, the pin 100 is pushed through both apertures 82, 86 and is irretrievably held between the moving head 80 and stationery head 90. The pin 100 is rotated via the use of a handle 106. After sterilization, when the practitioner wishes to retrieve the instruments within a container locked by the pin 100, the two heads 80, 90 are pulled apart. However, the pin 100 will not break if it is not oriented in a particular way. The pin 100 will only break when the blade 86 within the pin locker is aligned with the weakened region of the shaft 113, as depicted in FIG. 8a. If the blade is not aligned with the weakened region of the shaft 113, as depicted in FIG. 8b, the blade 86 will not be able to cut through the non-weakened area of the shaft 112, even when the practitioner attempts to pull the locking device heads 80, 90 apart. This design is advantageous because it allows the practitioner to close a compartment, lock the compartment with a pin and pin locker, and prevents the accidental opening of a sterilization container by forcing the practitioner to align a sterilization pin a particular orientation to break the pin to retrieve the instruments in the sterilization container.

While the invention has been described in terms of exemplary embodiments, it is to be understood that the words which have been used are words of description and not of limitation. As is understood by persons of ordinary skill in the art, a variety of modifications can be made without departing from the scope of the invention defined by the following claims, which should be given their fullest, fair scope.

I claim:

1. A multicompartment envelope for sterilization of medical or dental instruments, comprising:
    a plurality of compartments;
    a first layer of a flexible sheet material;
    a second layer of a flexible sheet material overlapping said first layer, said first and second layers secured together along a plurality of lines to form said plurality of compartments having at least one open side;
    wherein said plurality of compartments are secured around at least two sides of a periphery and unbonded on at least one side of a periphery, providing a space for insertion of instruments;
    wherein said plurality of compartments comprise a plurality of compartments arranged in an x-direction and a plurality of compartments arranged in a y-direction;
    a flap secured to said first layer, said flap including an adhesive side, said adhesive side:
        i) seals said plurality of open sides of said plurality of compartments arranged in said x-direction,
        ii) seals said plurality of open sides of said plurality of compartments arranged in said y-direction, and
        iii) overlaps an entirety of said plurality of compartments; and,
    whereby instruments within any one compartment can be retrieved while maintaining sterility of instruments within other compartments.

2. The multicompartment envelope of claim 1, further comprising:
    an aperture within said first layer, said second layer, and said flap for insertion of a sterilization indicator device.

3. The multicompartment envelope of claim 1, wherein said flexible sheet material is permeable to sterilization gases while being impervious to contaminants.

4. The multicompartment envelope of claim 1, wherein said multicompartment envelope further comprises a plurality of apertures aligned along an edge of said multicompartment envelope for insertion of said multicompartment envelope into a ringed binder;
    whereby insertion of a plurality of multicompartment envelopes into a ringed binder enables easy organization of sterilized medical or dental instruments.

5. The multicompartment envelope of claim 1, wherein said plurality of compartments are at least four compartments.

6. A system for organizing sterilized instruments, comprising:
    a) a plurality of multicompartment envelopes, each of said plurality of multicompartment envelopes comprising:
        i) a plurality of compartments wherein arranged in an x-direction and a plurality of compartments arranged in a y-direction;
        ii) a first layer of a flexible sheet material;
        iii) a second layer of a flexible sheet material overlapping said first layer, said first and second layers secured together along a plurality of lines to form said plurality of compartments having at least one open side;
        iv) a flap secured to said first layer, said flap including an adhesive side, said adhesive side:
            A) seals said plurality of open sides of said plurality of compartments arranged in said x-direction,
            B) seals said plurality of open sides of said plurality of compartments arranged and,
            C) overlaps an entirety of said plurality of compartments;
    b) a plurality of dividers indicating contents of said plurality of multicompartment envelopes;
    c) a binder for insertion of said plurality of multicompartment envelopes, said binder comprising a plurality of aligned rings,
    whereby each multicompartment sterilization envelope has a plurality of instruments for use in a single procedure or a plurality of similar instruments, and
    whereby said dividers group said plurality of multicompartment sterilization envelopes into procedure groups or instrument groups, thereby simplifying the retrieval of multiple instruments for use during a procedure.

7. The system of claim 6, wherein each of said plurality of multicompartment envelopes comprises:

a plurality of apertures aligned along an edge of said multicompartment envelope for insertion of said multicompartment sterilization envelope into a ringed binder.

* * * * *